(12) United States Patent
Michaely

(10) Patent No.: US 7,828,719 B2
(45) Date of Patent: Nov. 9, 2010

(54) CONSTRICTION DEVICE FOR MALE ORGAN TO OBVIATE ERECTILE DYSFUNCTION

(76) Inventor: Eliyahu Michaely, 40 Ha'ziyonut St., 58517, Holon (IL)

( * ) Notice: Subject to any disclaimer, the term of this patent is extended or adjusted under 35 U.S.C. 154(b) by 189 days.

(21) Appl. No.: 12/067,294

(22) PCT Filed: Aug. 20, 2006

(86) PCT No.: PCT/IL2006/000966

§ 371 (c)(1),
(2), (4) Date: Mar. 19, 2008

(87) PCT Pub. No.: WO2007/043037

PCT Pub. Date: Apr. 19, 2007

(65) Prior Publication Data

US 2008/0262291 A1 Oct. 23, 2008

(30) Foreign Application Priority Data

Oct. 9, 2005 (IL) .................................. 171300

(51) Int. Cl.
*A61F 5/00* (2006.01)
(52) U.S. Cl. ........................................ 600/41

(58) Field of Classification Search ............ 600/38–41; 128/897, 898
See application file for complete search history.

(56) References Cited

U.S. PATENT DOCUMENTS

| 4,539,980 | A | * | 9/1985 | Chaney | ........................ 600/41 |
|---|---|---|---|---|---|
| 4,628,915 | A | * | 12/1986 | Chaney | ........................ 600/41 |
| 4,724,829 | A | | 2/1988 | Knapps | |
| 5,195,943 | A | * | 3/1993 | Chaney | ........................ 600/41 |
| 5,234,402 | A | | 8/1993 | Osbon | |
| 5,695,444 | A | | 12/1997 | Chaney | |
| 5,893,827 | A | | 4/1999 | Jaquez et al. | |
| 5,997,470 | A | | 12/1999 | Coates | |
| 6,926,666 | B2 | * | 8/2005 | Magee | ........................ 600/38 |
| 2005/0101835 | A1 | | 5/2005 | Magee | |

* cited by examiner

*Primary Examiner*—Samuel G Gilbert
(74) *Attorney, Agent, or Firm*—Martin Fleit; Paul D. Bianco; Fleit Gibbons Gutman Bongini & Bianco PL

(57) ABSTRACT

A constriction device (100) for a male organ (170) of a user comprising: a substantially portable base (110); at least two bands (140, 150), each comprising of an elastic central ring (141, 151) tightly adjustable onto said base; each elastic central ring (141, 151) tightly encircling male organ (170) upon releasing the corresponding band (140, 150) from base (110), thereby substantially avoiding back-flow of blood out of the male organ (170) and therefore improving erection of male organ (170).

11 Claims, 10 Drawing Sheets

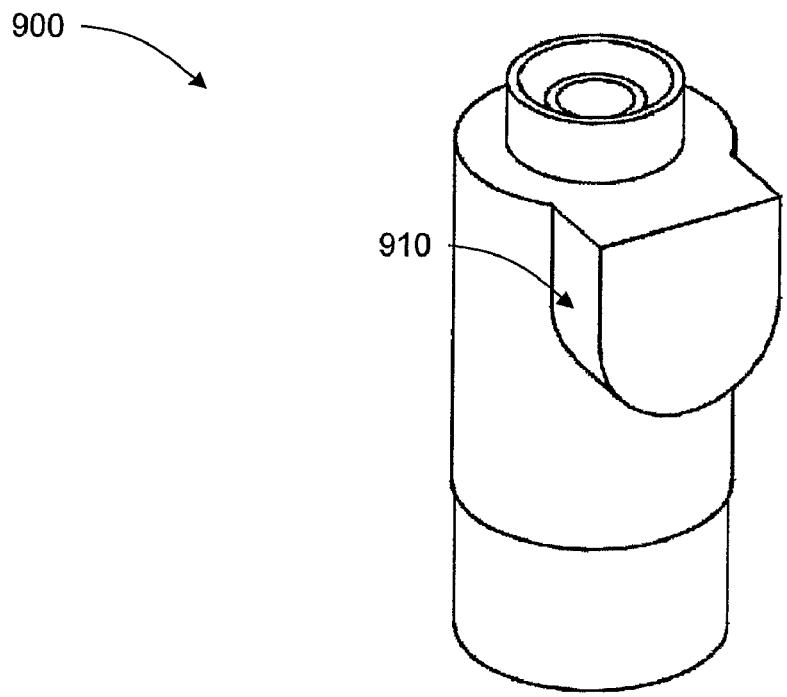
Figure 9a
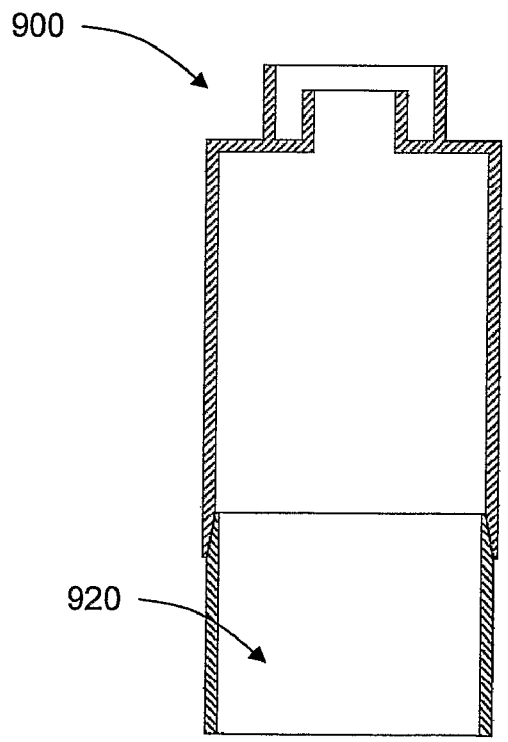 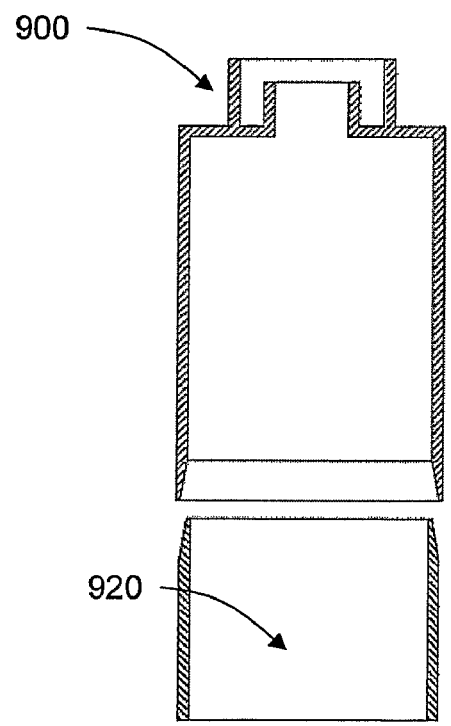
Figure 9bFigure 9c

# CONSTRICTION DEVICE FOR MALE ORGAN TO OBVIATE ERECTILE DYSFUNCTION

BACKGROUND OF THE INVENTION

In the art, several male organ constriction devices and methods of using such devices were presented, designed for obviating male erectile dysfunction. Such devices provide constriction of the male organ only at one location. Providing constriction of the male organ at only one location may be insufficient in order to obtain an erection that is lasting enough during sexual intercourse.

A male organ constriction devices and the methods of using such devices have been disclosed by Chaney, "Male organ constriction device and method of using the device", U.S. Pat. No. 5,695,444; by Magee, "Penile tension system, device, kit, and methods of using same", patent application number US2005101835; by Coates, "Penile tube and constriction ring removal guide system and method of use", U.S. Pat. No. 5,997,470; by Osbon, "Apparatus and method for augmenting male potency with user tissue protection" U.S. Pat. No. 5,234,402; by Knapps, "Anatomical aid", U.S. Pat. No. 4,724,829 and by Jaquez, "Device for obviating erectile dysfunctioning", U.S. Pat. No. 5,893,827. Implementations of the above-mentioned patent applications provide constriction of the male organ at one location only.

SUMMARY OF SOME EMBODIMENTS OF THE INVENTION

In embodiments of the invention, a constriction device for male organ of a user comprises a substantially portable base; at least two bands, each comprising of an elastic central ring that is tightly adjustable onto the base; each elastic central ring tightly encircling the male organ upon releasing the corresponding band from the base, thereby substantially avoiding back-flow of blood out of the male organ and therefore improving erection of the male organ.

In embodiments of the invention, the constriction device for male organ includes at least one C-shaped handle that is fixedly attached to each of the elastic central rings, thereby providing a handle for releasing the bands from the base onto the male organ.

In embodiments of the invention, each C-shaped handle enables the user to adjust the corresponding band on the male organ.

In embodiments of the invention, each C-shaped handle is further connected by a Y-shaped connector to the central elastic band, thereby enabling pulling the central elastic rubber band at multiple points.

In embodiments of the invention, the constriction device comprises a cord connected to at least one of the C-shaped handles, the cord enabling longitudinally adjusting the elastic central rubber band on the male organ.

In embodiments of the invention, the cord is designed to be wrapped around a human body part such as, e.g., a shoulder.

In embodiments of the invention, the constriction device comprises a cutting tool comprising of two parts that are slidably connected to each other, wherein one part includes a cutting blade enabling cutting the elastic central band by pulling the two parts contrarily relative to each other.

In embodiments of the invention, the constriction device for male organ may be used by the user by performing the following steps: fitting a first elastic central ring and a second elastic central ring onto the base; fitting the base over the male organ such that the first elastic central ring is closer to the user's abdomen than the second elastic central ring; releasing the first elastic central ring from the base onto the male organ by pulling the corresponding C-shaped handle, such that the first elastic central ring is located between the user's abdomen and the base; turning the base; fitting the base again over the male organ; releasing the second elastic central ring from the base onto the male organ, by pulling the corresponding C-shaped handle such that the second elastic is fitted between the first central ring and the user's abdomen; connecting a cord to each of the corresponding C-shaped handles; and adjusting the first and the second central elastic central ring by pulling the cord accordingly.

BRIEF DESCRIPTION OF THE DRAWINGS

The subject matter regarded as the invention will become more clearly understood in light of the ensuing description of embodiments herein, given by way of example and for purposes of illustrative discussion of the present invention only, with reference to the accompanying drawings, wherein

FIG. 7b is a schematic illustration of the band while stretched according to an embodiment of FIG. 6a;

FIG. 8b is a schematic illustration of an isometric view of the band according to an embodiment of FIG. 8a;

FIG. 9a is an isometric view of a vacuum pump supplement, according to an embodiment of the invention;

FIG. 9b is cross-sectional side view of the vacuum pump supplement, according to an embodiment of the invention;

FIG. 9c is a cross-sectional side view of the unjointed vacuum pump supplement, according to an embodiment of the invention;

Figure 1:
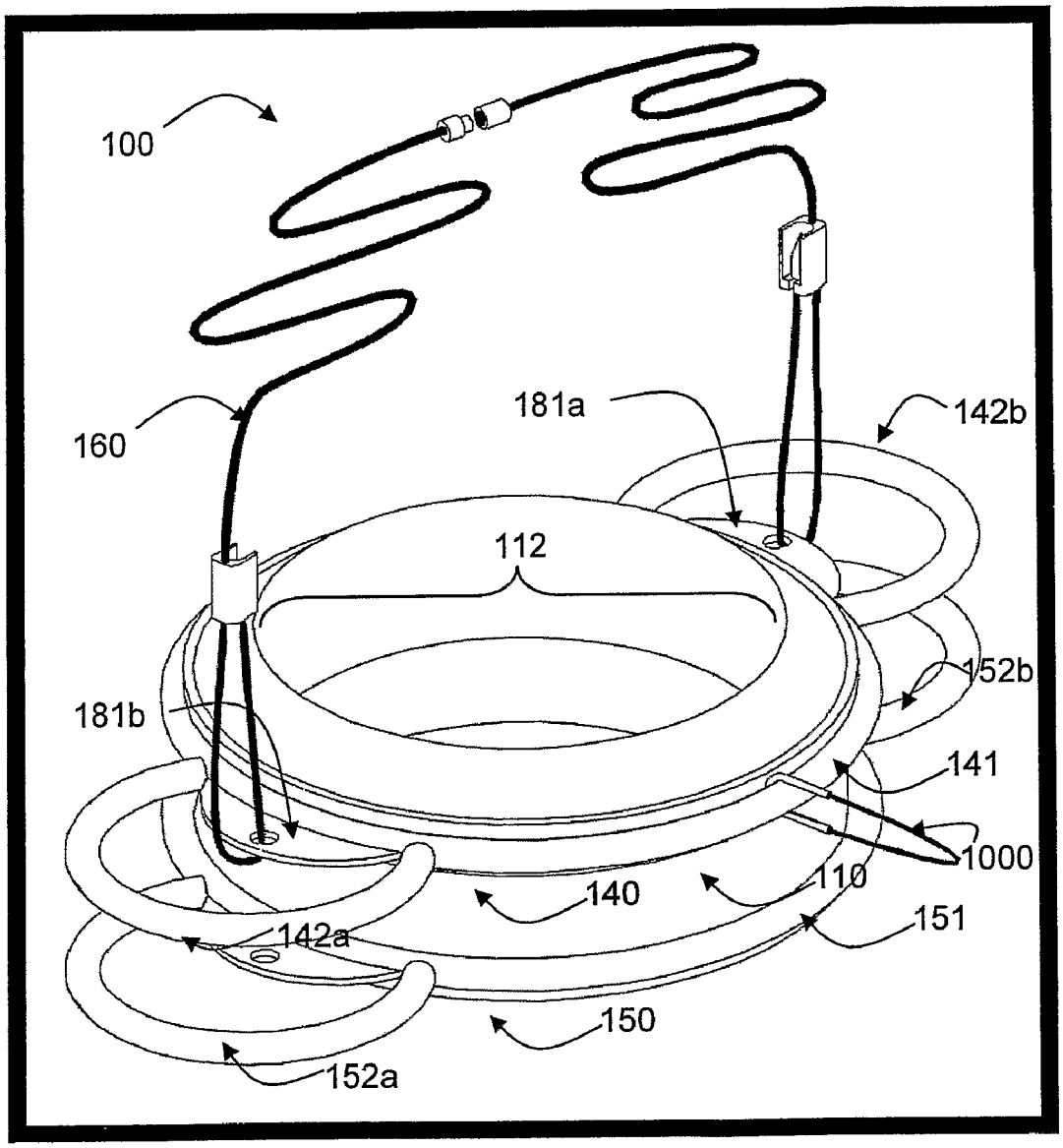
FIG. 1 is an isometric illustration of a male constriction device, according to an embodiment of the invention.

The drawings taken with description make apparent to those skilled in the art how the invention may be embodied in practice. It should be understood that no attempt is made to show structural details of the invention in more detail than is necessary for a fundamental understanding of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF EMBODIMENTS OF THE INVENTION

The present invention relates to a novel constriction device and method for a male organ to substantially obviate erectile dysfunction. The device enables constriction of a male organ at a plurality of location, thereby enabling better adjustment of the blood flow according to the physiological functionality of the male organ. Therefore, erection of the male organ is substantially ameliorated.

An embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "one embodiment", "an embodiment", "some embodiments" or "other embodiments" means that a particular feature, structure, or characteristic described in connection with the embodiments is included in at least one embodiment, but not necessarily all embodiments, of the inventions.

It is understood that the phraseology and terminology employed herein is not to be construed as limiting and is for descriptive purpose only.

The principles and uses of the teachings of the present invention may be better understood with reference to the accompanying description, figures and examples.

It is to be understood that the details set forth herein do not construe a limitation to an application of the invention. Furthermore, it is to be understood that the invention can be carried out or practiced in various ways and that the invention can be implemented in embodiments other than the ones outlined in the description below.

It is to be understood that the terms "including", "comprising", "consisting" and grammatical variants thereof do not preclude the addition of one or more components, features, steps, integers or groups thereof and that the terms are not to be construed as specifying components, features, steps or integers.

The phrase "consisting essentially of", and grammatical variants thereof, when used herein is not to be construed as excluding additional components, steps, features, integers or groups thereof but rather that the additional features, integers, steps, components or groups thereof do not materially alter the basic and novel characteristics of the claimed composition, device or method.

If the specification or claims refer to "an additional" element, that does not preclude there being more than one of the additional element.

It is to be understood that where the claims or specification refer to "a" or "an" element, such reference is not to be construed as there being only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" refers to manners, means, techniques and procedures for accomplishing a given task including, but is not limited to those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention can be implemented in the testing or practice with methods and materials equivalent or similar to those described herein.

The terms "bottom", "below", "top" and "above" as used herein do not necessarily indicate that a "bottom" component is below a "top" component, or that a component that is "below" is indeed "below" another component or that a component that is "above" is indeed "above" another component. As such, directions, components or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain components, to indicate a first and a second component or to do both.

Figure 2A:
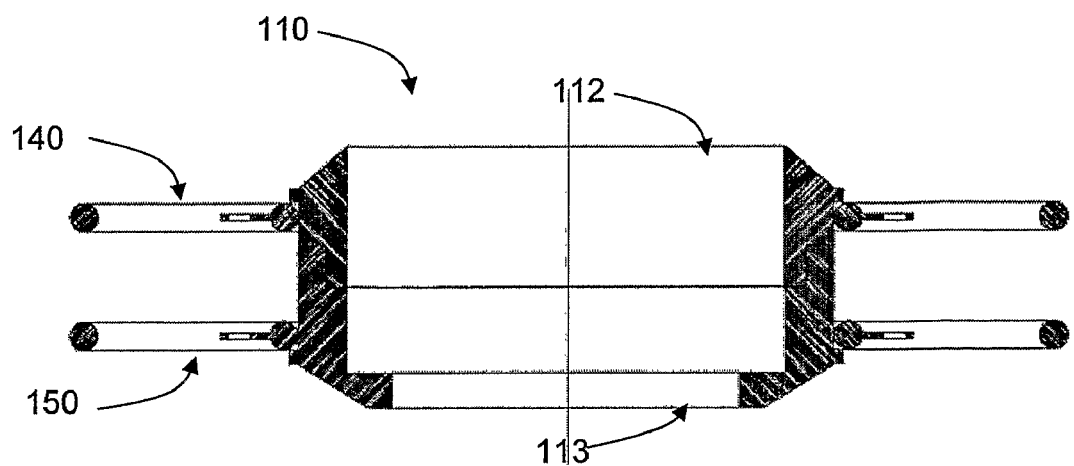
FIG. 2a is a schematic illustration of a side view of the device, according to an embodiment of the invention.
Figure 2B:
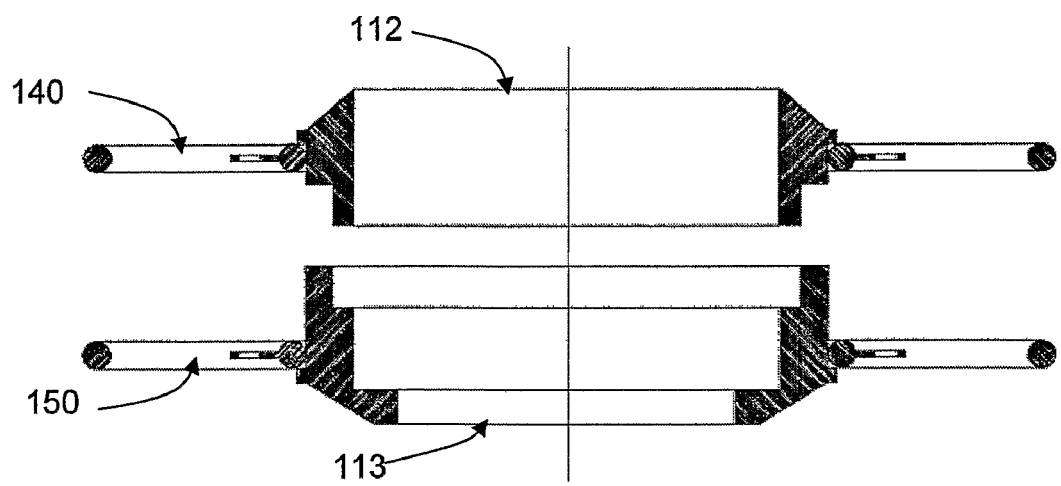
FIG. 2b is a schematic illustration of a side view of the unjointed device, according to an embodiment of the invention.
Figure 3:
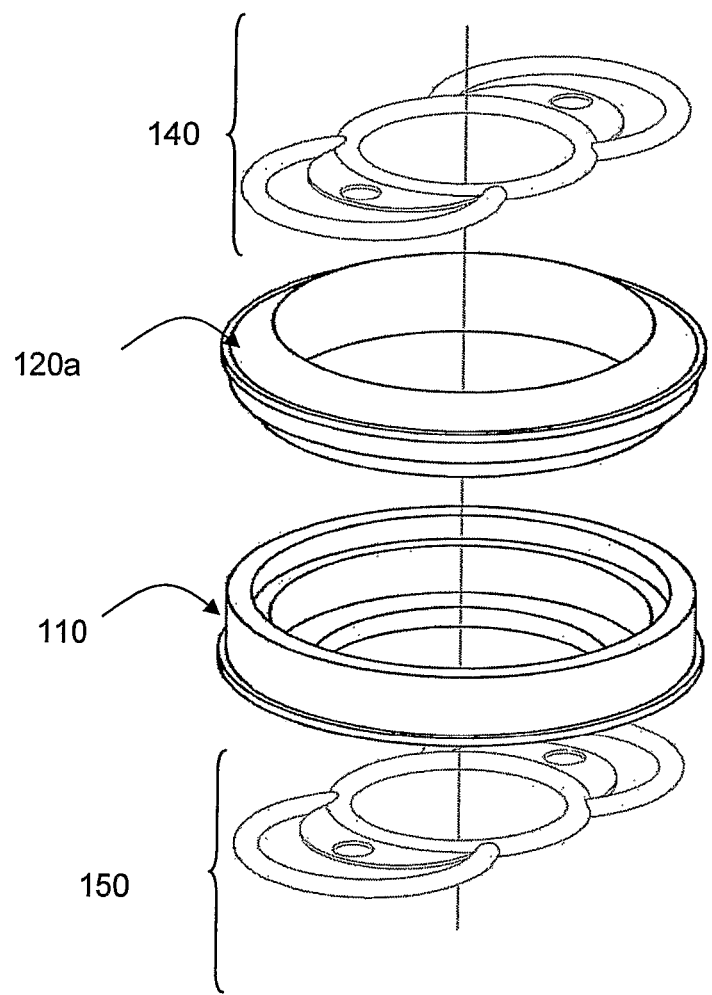
FIG. 3 is an isometric assembling illustration of the device according to an embodiment of the invention.

Reference is now made to FIG. 1, which is an isometric illustration of a male constriction device according to an embodiment of the invention; to FIG. 2a, which schematically illustrates a side view of the device, according to an embodiment of the invention; to FIG. 2b, which schematically illustrates a side view of the unjointed device, according to an embodiment of the invention; and to FIG. 3, which schematically illustrates an isometric assembling illustration of the device according to an embodiment of the invention.

According to some embodiments of the invention, an erection sustaining device 100 (hereinafter referred to as "device") includes a portable base 110, which may comprise of two portable parts 112 and 113. It is to be understood that base 110 may have various cross-sectional geometries such as, e.g., circular, rectangular and the like.

In an embodiment of the invention, an inner side 111 of base 110 may have various diameters suitable for fitting base 110 over any human sexual male organ. The diameter may range for example, from 2 cm to 5 cm.

Base 110 may be made of various suitable materials such as, e.g., plastic, silicon and the like. Furthermore, base 110 may comprise of a plurality of detachable parts, thereby facilitating portability.

According to some embodiments of the invention; device 100 is adapted to fit a plurality of bands such as band 140 and band 150, over male organ 170. Band 140 and/or 150 may comprise of an elastic central ring 141 and 151, respectively. Elastic central 141 and/or 151 ring may be made out of rubber or any other suitable material that provides elasticity. Elastic central ring 141 may have two C-shaped handles 142a and 142b fixedly attached thereto, located substantially opposite to each other. Similarly, elastic central ring 151 may have two C-shaped handles 152a and 152b fixedly attached thereto, located substantially opposite to each other. C-shaped handles 142a, 142b, 152a and 152b may be made of rubber, plastic or any other suitable material.

According to some embodiments of the invention, base 110 may have regressions (not shown), respectively, along their perimeter, into which central elastic ring 141 and 151 ring may be fitted in an outstretched manner, respectively.

According to some embodiments of the invention, base 110 is placed over male organ 170 of the user, such that device 100 abuts the abdomen of the user. The user may then release band 140 from base 110 by pulling C-shaped handles 142a and 142b. Upon releasing bands 140 from base 110, elastic central ring 141 is fitted tightly over male organ 170, thereby substantially constricting backflow of blood from male organ 170. Male organ 170 may be caused to be aroused by the user by pressing handles 142a, 142b of device 100 repeatedly against the abdomen, bending central ring 141 to admit blood, under pressure from the heart, into the organ. Other methods for arousing male organ 170 may additionally be used. Base 110 may then be removed from male organ 170, turned around and put again over male organ 170. The user then releases central elastic ring 151 over male organ 170 by pulling C-shaped handles 152a and 152b, such that band 150 is positioned between band 140 and the user's abdomen, whereby base 110 is again pressed repeatedly against the abdomen and handles 142a, 142b and 152a, 152b to alternately bend central rings 141 and 151, thereby alternately admitting blood between and past rings 141 and 151, to further increase stiffness of male organ 170. As a consequence, blood flow into male organ 170 is increased, and blood flow from male organ 170 is further constricted, thereby generating a lasting erection of male organ 170.

According to some embodiments of the invention, device 100 may further include a cutting tool 1000 that enables cutting elastic central ring 140 and/or 150 during e.g., sexual intercourse, as will be outlined in detail below with reference to FIGS. 10a and 10b.

Figure 4:
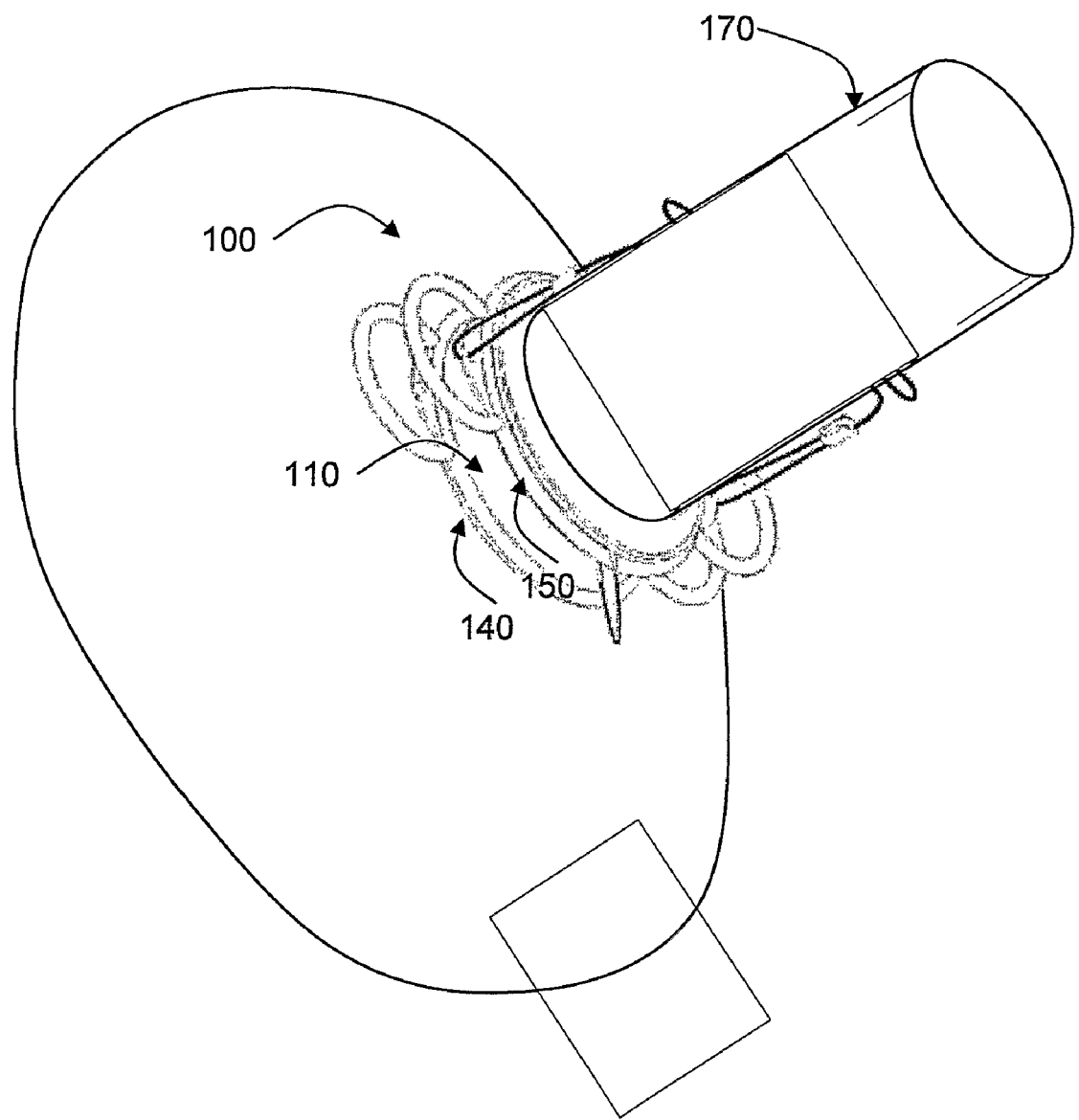
FIG. 4 is an isometric illustration of a male organ engaged with the device, according to an embodiment of the invention.
Figure 5A:
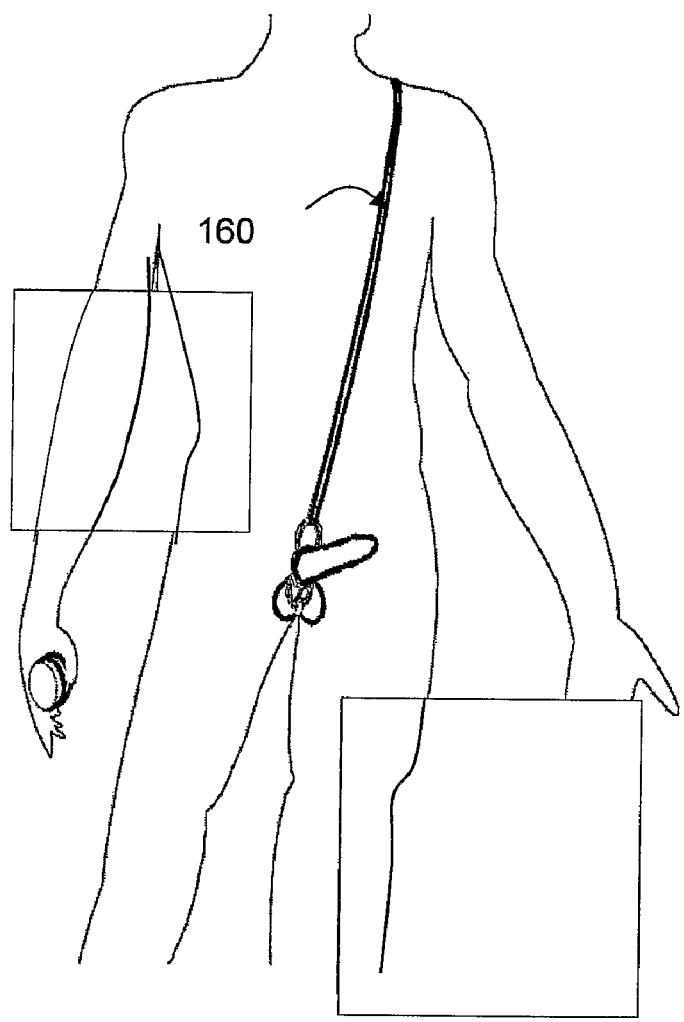
FIG. 5a is a schematic illustration of a band engaged with a male organ, according to an embodiment of the invention.
Figure 5B:
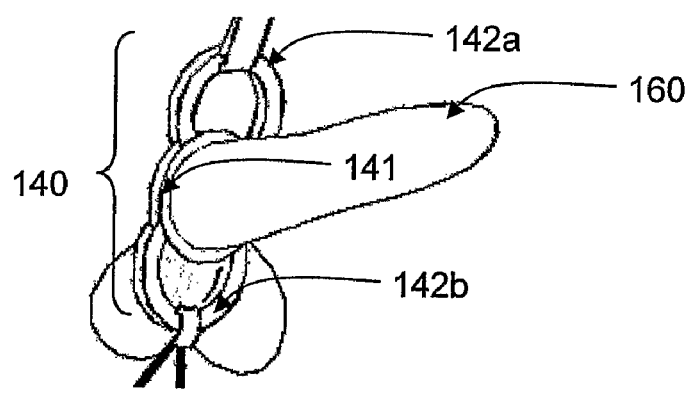
FIG. 5b is a detailed schematic illustration of a band engaged with a male organ, according to an embodiment of the invention.
Figure 6:
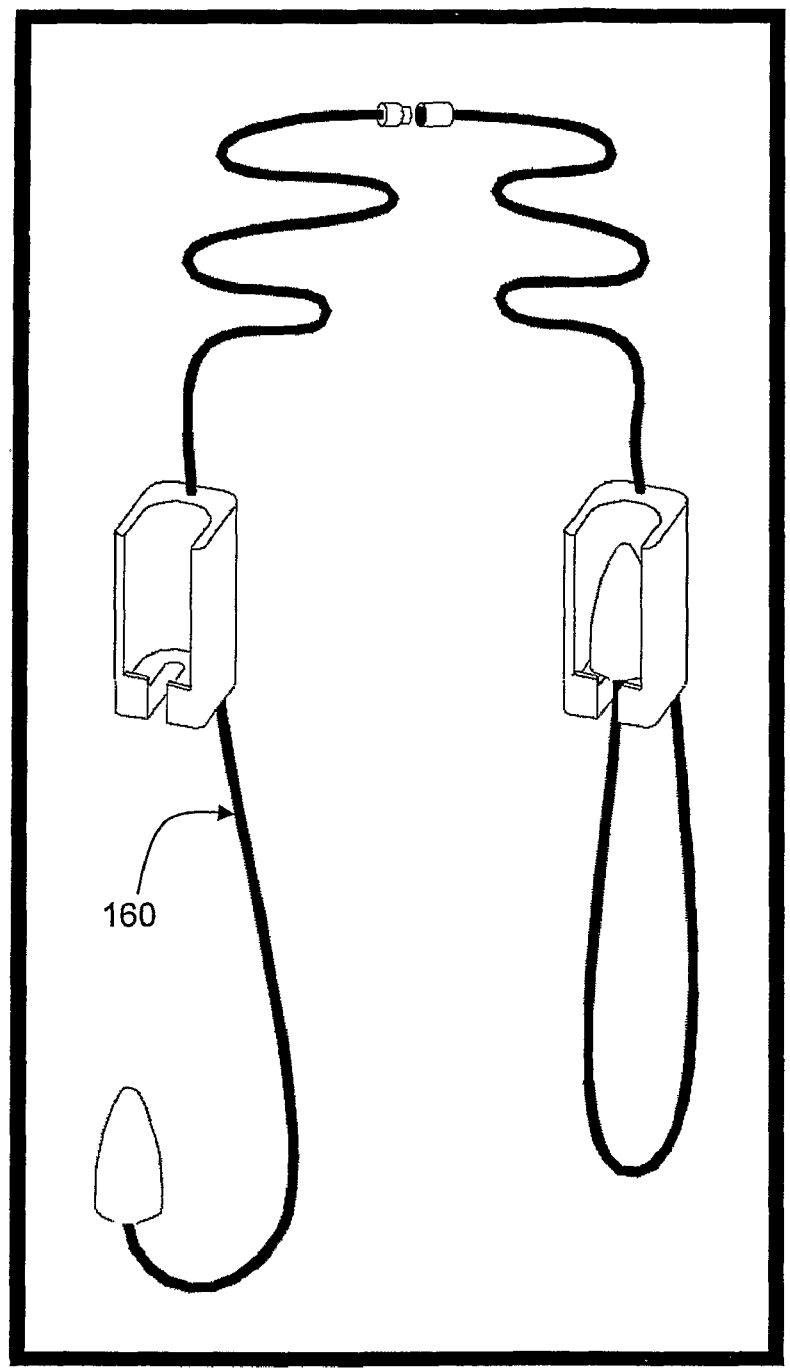
FIG. 6 is a schematic illustration of a cord arrangement according to an embodiment of the invention.

Reference is now made to FIG. 4, which schematically illustrates the male organ engaged with the device according to an embodiment of the invention; to FIG. 5a, which is a schematic isometric illustration of bands engaged with a male organ, according to an embodiment of the invention; to FIG. 5b, which is a detailed schematic illustration of a band engaged with a male organ, according to an embodiment of the invention and to FIG. 6, which schematically illustrates a cord arrangement according to an embodiment of the invention.

According to some embodiments of the invention, a cord 160, which may be made of any suitable material such as, e.g., silicon, rubber, plastic, fabric and the like, may be connected or tied onto each of the C-shaped handles 142a and 152a. Connecting cord 160 to each of the corresponding C-shaped handles may enable the user to longitudinally adjust each central elastic ring 141 and/or 151 by pulling the cord accordingly.

Cord 160 may be connected to central elastic ring 141 and/or 151 via half-moon shaped elements 181a and/or 181b, according to some embodiments of the invention.

Figure 7A:
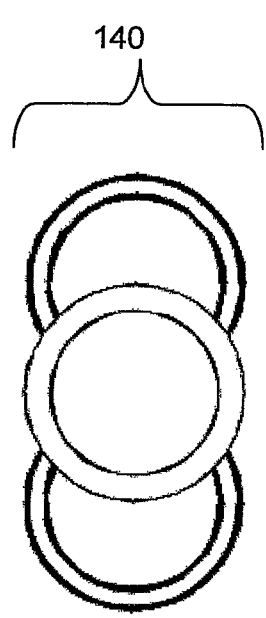
FIG. 7a is a schematic illustration of a band according to an embodiment of the invention.
Figure 7B:
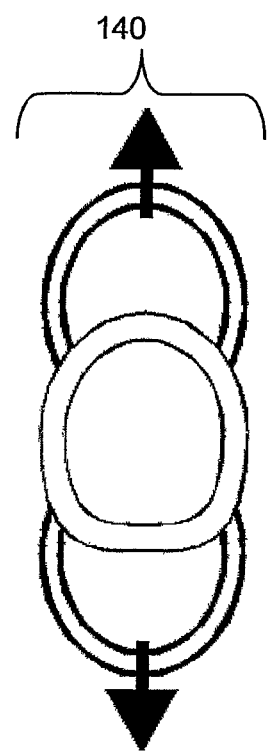
Figure 7C:
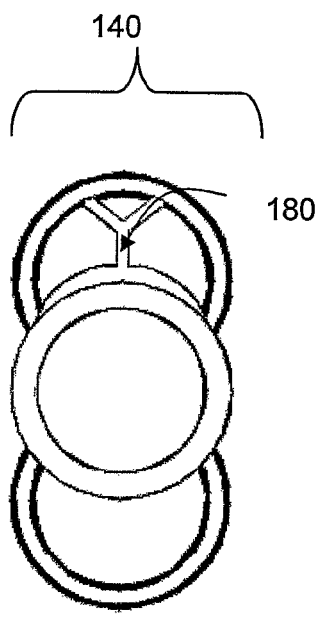
FIG. 7c is a schematic illustration of a band according to another embodiment of the invention.
Figure 7D:
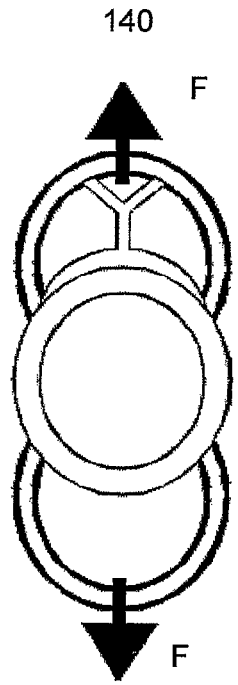
FIG. 7d is a schematic illustration of the band according to the embodiment of FIG. 6c.

Reference is now made to FIG. 7a, which schematically illustrates bands 140 and 150 according to embodiments of the invention; and to FIG. 7b, which schematically illustrates the elastic band while stretched according to an embodiment of FIG. 7a. In addition, reference is made to FIG. 7c, which schematically illustrates a band comprising a Y-connector according to another embodiment of the invention; and to FIG. 7d, which schematically illustrates the band according to the embodiment of FIG. 7c;

According to another embodiment of the invention, user of band 140 and/or 150 may want to adjust the bands on male organ 170. This may be accomplished by pulling, e.g., C-shaped handle 142a and/or 152a, respectively. However, pulling C-shaped handle 142a and/or 152a may be inefficient in adjusting band 140 and/or 150, respectively. Therefore, in some embodiments of the invention, band 140 and/or 150 may include various features that facilitate adjustment of band 140 and/or 150. For example, band 140 may comprise a Y-shaped connector 180 that provides additional connecting points between elastic central ring 141 and C-shaped handles 142a. Due to Y-shaped connector 180, pulling for example, results in C-shaped handle 142a may pull central elastic ring 141 at three locations, thereby providing additional balance in pulling central elastic ring 140. This is in contrary to the embodiment shown in FIG. 6b, in which central elastic ring 141 is pulled only at two locations.

Figure 8A:
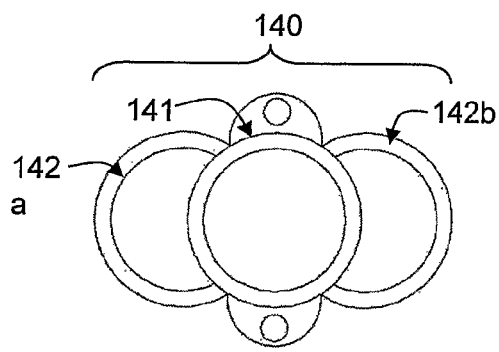
FIG. 8a is a schematic illustration of a top view of a band according to an embodiment of the invention.
Figure 8B:
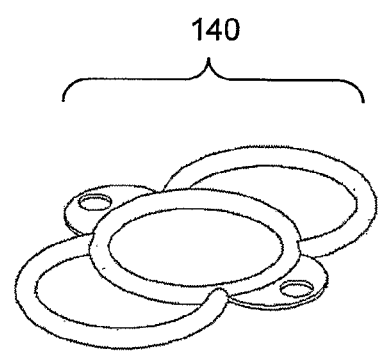
Figure 8C:
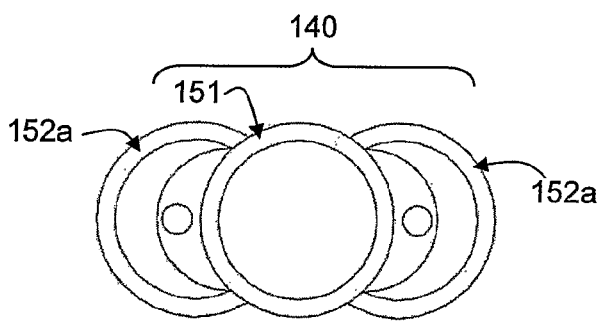
FIG. 8c is a schematic illustration of a top view of another band according to an embodiment of the invention.
Figure 8D:
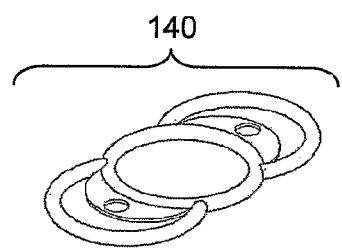
FIG. 8d is a schematic illustration of an isometric view of the band according to an embodiment of FIG. 8c.
Figure 8E:
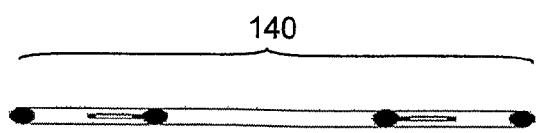
FIG. 8e is a schematic illustration of a side view of the band according to an embodiment of FIG. 8c.

FIG. 8a schematically illustrates a top view of an elastic band according to an embodiment of the invention;

FIG. 8b schematically illustrates an isometric view of the elastic band according to an embodiment of the invention;

FIG. 8c schematically illustrates a top view of another elastic band according to an embodiment of the invention;

FIG. 8d schematically illustrates an isometric view of the elastic band according to an embodiment of FIG. 8c;

FIG. 8e schematically illustrates a side view of the elastic band according to an embodiment of FIG. 8c;

Reference is now made to FIG. 9a, which schematically illustrates an isometric view of a vacuum pump, according to an embodiment of the invention.

According to some embodiments of the invention, device 100 may be used in conjunction with a vacuum pump 900. Male organ 170 may be inserted into the vacuum pump. By operating the vacuum pump, blood may be sucked into male organ 170, thereby causing 170 to erect. Device 100 may then again be applied onto male organ 170

According to some embodiments of the invention, vacuum pump 900 may have a protrusion 910. Protrusion 910 enables male organ 170 to extend during the erection without being confined by a side wall of vacuum pump 900.

Reference is now made to FIG. 9b, which schematically illustrates a cross-sectional side view of the pump supplement, according to an embodiment of the invention and to FIG. 9c, which schematically illustrates a cross-sectional side view of the unjointed pump supplement, according to an embodiment of the invention.

In some embodiments of the invention, vacuum pump 900 may include a modularly attachable part 920, which may have various diameters. Therefore, vacuum pump 900 may be engaged with various male organs, each male organ having a different diameter.

Figure 10A:
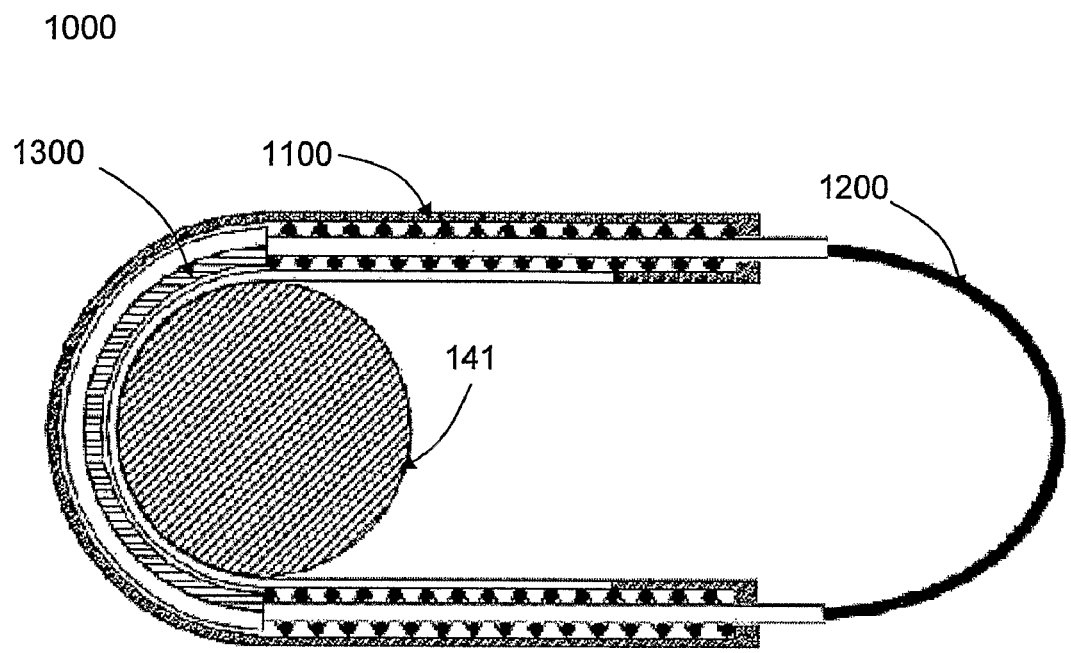
FIG. 10a schematically illustrates a cutting tool according to an embodiment of the invention.
Figure 10B:
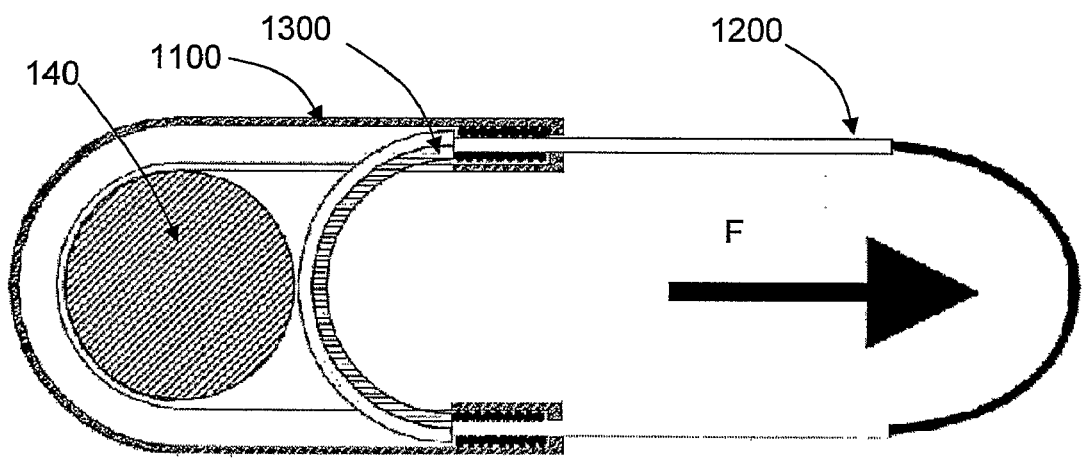
FIG. 10b schematically illustrates the operation of cutting using the cutting tool according to an embodiment of the invention.

Reference is now made to FIG. 10a, which schematically illustrates a cutting tool according to an embodiment of the invention. Additional reference is made to FIG. 10b, which schematically illustrates the operation of cutting using the cutting tool according to an embodiment of the invention.

In some embodiments of the invention, the user of device 100 may want to release band 140 and/or band 150 from male organ 170 using a short procedure such as, e.g., cutting band 140 and/or 150. For this purpose a cutting tool 1000 is introduced, which may comprise of two parts 1100 and 1200 that are slidably connected to each other. Part 1200 has a cutting blade 1300 able to cut material such as rubber. Therefore, the user may use cutting tool 1000 to cut elastic central band 141 and/or 151 by pulling part 1200 away from part 1100, as schematically indicated with arrow F.

While the invention has been described with respect to a limited number of embodiments, these should not be construed as limitations on the scope of the invention, but rather as exemplifications of some of the possible embodiments. Those skilled in the art will envision other possible variations, modifications, and applications that are also within the scope of the invention.

What is claimed is:

1. A constriction device for male organ of a user, said device comprising:
    a substantially portable base sized and dimensioned to encircle the organ at a base of the organ;
    at least two bands, each comprising an elastic central ring sized and dimensioned to resiliently encircle the organ, the central rings mountable onto said base;
    each elastic central ring operative to tightly encircling the male organ upon being demounted from said base, thereby substantially avoiding back-flow of blood out of said male organ and therefore improving erection of said male organ; and
    a cutting tool surrounding at least a portion of at least one of said elastic central band, comprising of two parts that are slidably connected to each other, wherein one part includes a cutting blade enabling cutting said elastic central band by pulling one part away from the other part.

2. The constriction device for male organ of claim 1, wherein at least one C-shaped handle is fixedly attached to each of the elastic central rings, thereby providing a handle for releasing said bands from the base onto the male organ.

3. The constriction device for male organ of claim 2, wherein each C-shaped handles is further connected by a Y-shaped connector to said central elastic band, thereby enabling pulling said central elastic rubber band at multiple points.

4. The constriction device for male organ of claim 1, wherein each C-shaped handle enables the user to adjust the corresponding band on the male organ.

5. The constriction device of claim 1, further comprising a cord connected to at least one of the C-shaped handles, said cord enabling longitudinally adjusting said elastic central rubber band on said male organ.

6. The constriction device of claim 5, wherein said cord is designed to be wrapped around a human body part.

7. The constriction device of claim 1, wherein the device is adapted to be used by said user by performing the following steps:
    a) fitting a first elastic central ring and a second elastic central ring onto said base;
    b) fitting the base over the male organ such that the first elastic central ring is closer to the user's abdomen than the second elastic central ring;
    c) releasing said first elastic central ring from the base onto the male organ by pulling the corresponding C-shaped handle, such that the first elastic central ring is located between the user's abdomen and the base;
    d) turning the base
    e) fitting the base again over the male organ
    f) releasing said second elastic central ring from the said base onto the male organ, by pulling the corresponding C-shaped handle such that said second elastic is fitted between said first central ring and the user's abdomen;
    g) connecting a cord to each of the corresponding C-shaped handles;
    and adjusting said first and said second central elastic central ring by pulling said cord accordingly.

8. A device for generating and maintaining an erection of the sexual organ of a male, comprising:
    at least two resilient bands sized to encircle the organ, thereby operative in a constricting position to restrict a flow of blood into or out of the organ, each of said at least two resilient bands having at least one extension extending away the organ when said at least two resilient bands encircle the organ;
    a supporting ring sized to encircle the organ, the supporting ring operative to support said at least two resilient bands at a diameter larger than the diameter of the organ, thereby facilitating positioning of said at least two resilient bands onto the organ, the supporting ring further operative to enable the release of said at least two supporting rings onto the organ,
    the supporting ring having a diameter greater than said at least two resilient bands when said at least two resilient bands are in said constricting position, the supporting ring further having a diameter less than a diameter defined by a radial extent of said at least one extension, the supporting ring operative thereby to be pressed against the abdomen of the male thereby contacting said at least one extension of at least one of said at least two resilient bands, thereby bending at least one of said at least two resilient bands, thereby permitting blood flow into the organ, and blocking blood flow when said supporting ring is not pressed.

9. The device of claim 8, wherein said at least one extension has the form of a C-shaped handle.

10. A method of generating and maintaining an erection of the sexual organ of a male, comprising:
    mounting at least two resilient bands on a base sized and dimensioned to encircle the root of the organ;
    demounting said at least two resilient bands onto the organ whereby said bands are operative to restrict blood flow into or out of the organ;
    pressing said base against at least one of said at least two resilient bands to bend said at least one resilient band to enable blood to flow into the organ;
    releasing said base from against said at least one of said at least two resilient bands, to restrict blood flow out of the organ;
    repeating said pressing and releasing steps until a desired erection is generated and maintained.

11. The method of claim 10, wherein blood is trapped between a first of said at least two resilient bands after said step of pressing, said trapped blood released into the organ after a subsequent pressing step.

* * * * *